United States Patent [19]
Clarke et al.

[11] Patent Number: 5,114,403
[45] Date of Patent: May 19, 1992

[54] CATHETER TORQUE MECHANISM

[75] Inventors: Ray Clarke, Los Altos; Matthew S. Solar, Sunnyvale, both of Calif.

[73] Assignee: Eclipse Surgical Technologies, Inc., Palo Alto, Calif.

[21] Appl. No.: 407,462

[22] Filed: Sep. 15, 1989

[51] Int. Cl.$^5$ .............................................. A61M 29/00
[52] U.S. Cl. ........................................ 604/96; 604/95; 606/194
[58] Field of Search ...................... 604/95, 96; 606/194

[56] References Cited

U.S. PATENT DOCUMENTS

| | | | |
|---|---|---|---|
| 4,419,095 | 12/1983 | Nebergall et al. | 604/96 |
| 4,758,221 | 7/1988 | Jureidini | 604/96 |
| 4,770,653 | 9/1988 | Shturman | 604/96 |
| 4,874,371 | 10/1989 | Comben et al. | 604/95 |
| 4,898,577 | 2/1990 | Badger et al. | 604/95 |
| 4,920,980 | 5/1990 | Jackowski | 604/95 |

*Primary Examiner*—Richard J. Apley
*Assistant Examiner*—Lynne Reichard
*Attorney, Agent, or Firm*—Owen, Wickersham & Erickson

[57] ABSTRACT

A torque control mechanism for a medical catheter, comprising a torque wire affixed to a tip of the catheter, and attached to a rotation control mechanism carried by a proximal end of the catheter. The torque wire has high torsional stiffness but longitudinal flexibility, so that rotation of the torque wire is efficiently transmitted to the catheter tip, but so that the torque wire may flex easily as the catheter is put into place adjacent a treatment site within a patient. The catheter tip includes a guide wire lumen for sliding over a conventional guide wire in emplacing the catheter, and rotation of the torque wire causes the catheter tip to rotate about an axis of the guide wire. However, when high friction is encountered by the catheter, rotation of the torque wire causes rotation of the catheter tip about a central axis of the catheter. This is assisted by the configuration of a preferred embodiment, wherein the catheter tip is rotatable separately from the catheter body.

The rotation mechanism includes a handle which is threaded into a swivel housing, and rotational motion of the handle is limited by stops. A threaded nut may be slidably positioned on the handle, for converting rotational motion of the handle into translational motion of the nut, which engages the stops for limiting the rotational motion of the handle, and which allows rotation of the handle to result in purely rotational motion of the torque wire, with no translational component.

4 Claims, 8 Drawing Sheets

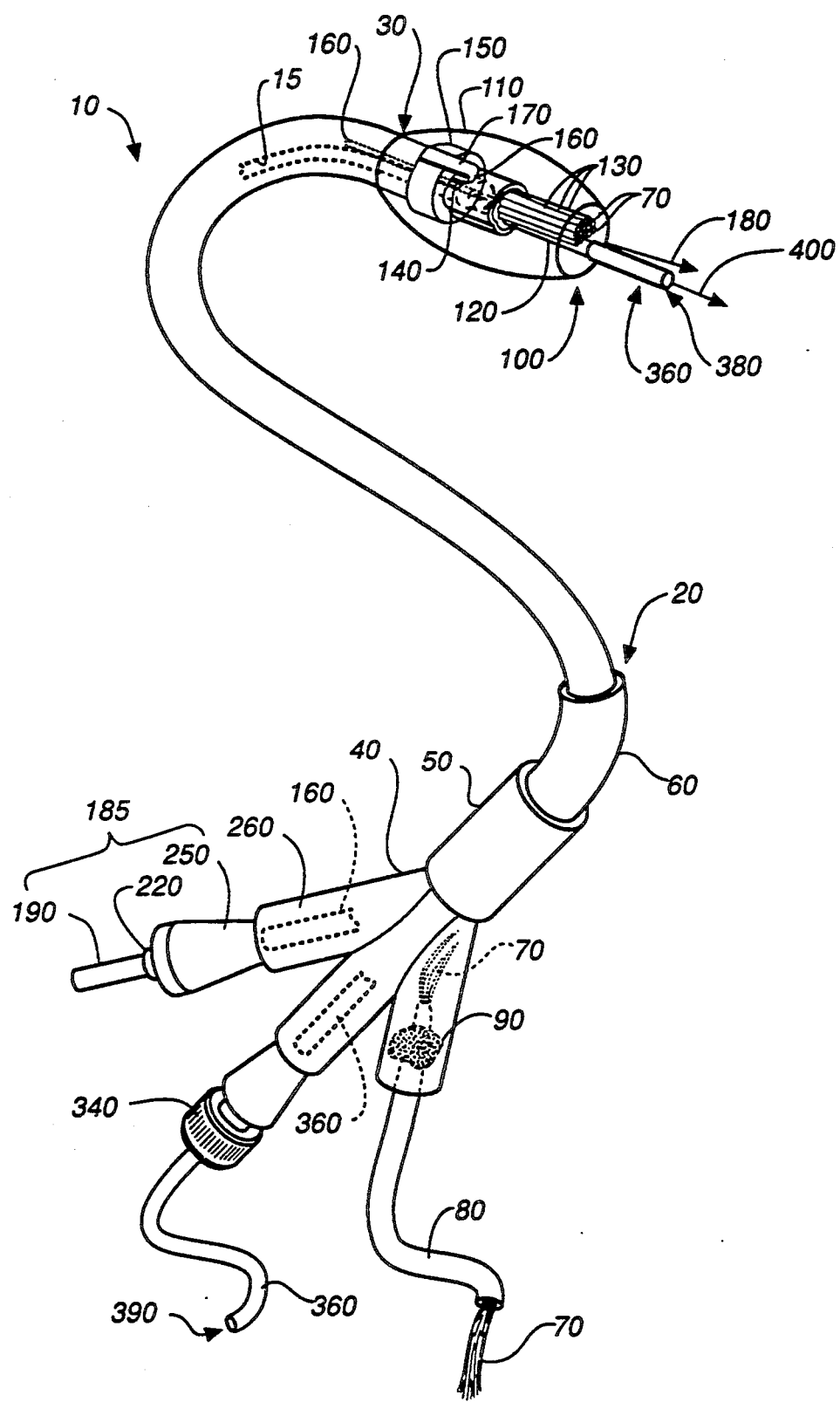
FIG._1

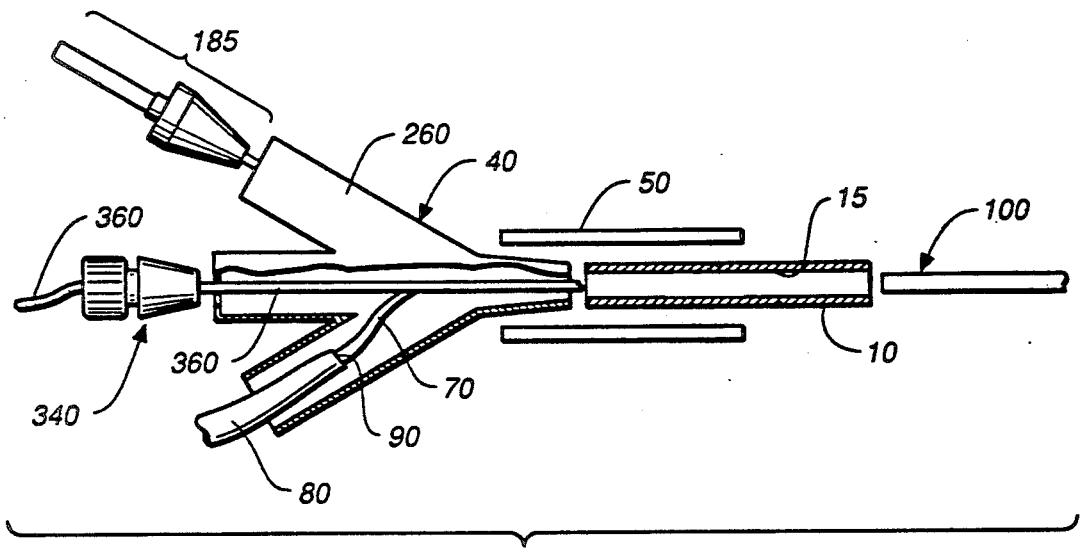
FIG._2
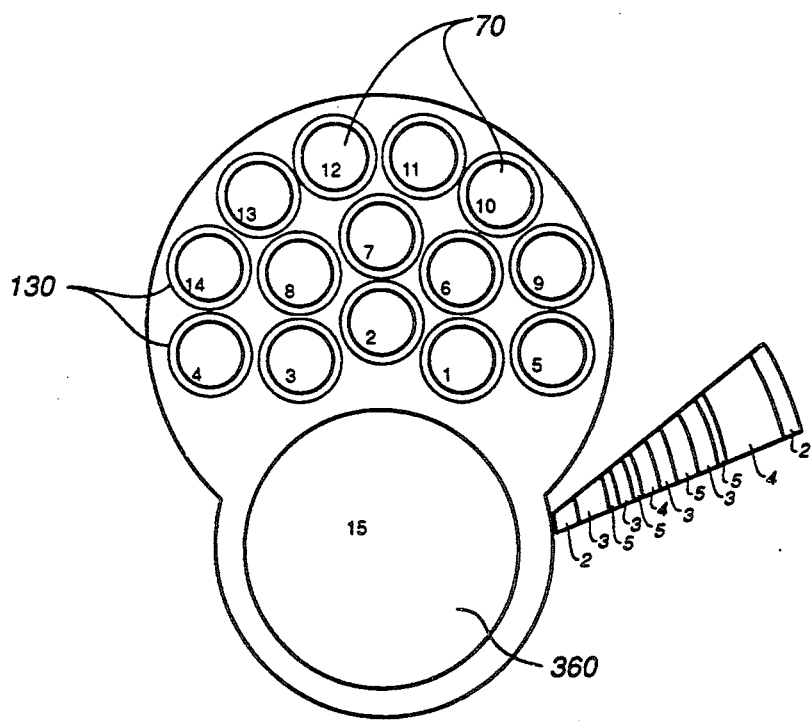
FIG._3A

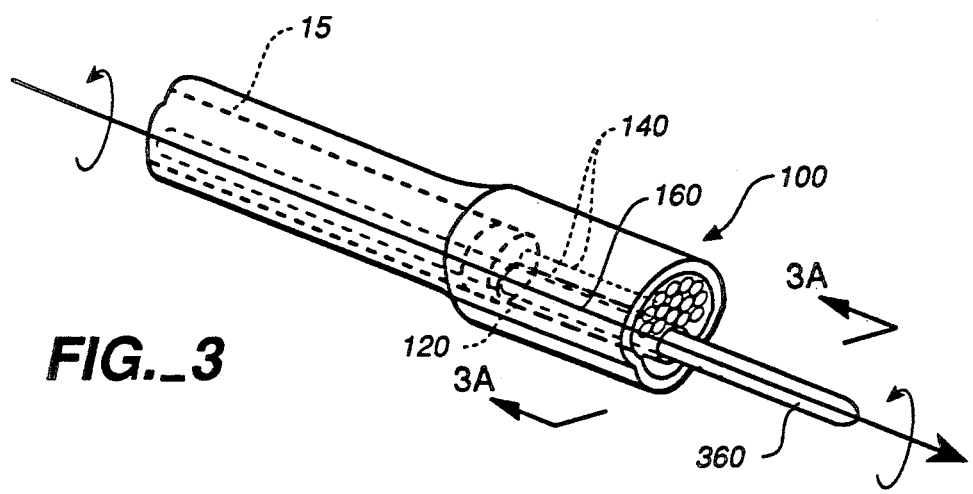
FIG._3
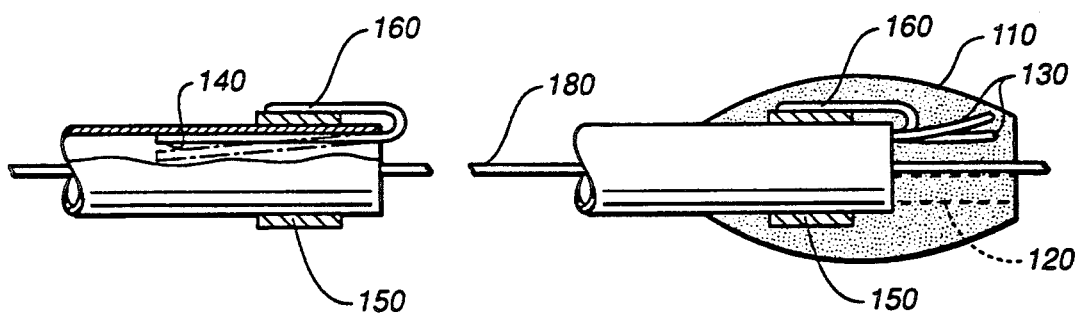
FIG._4  FIG._5
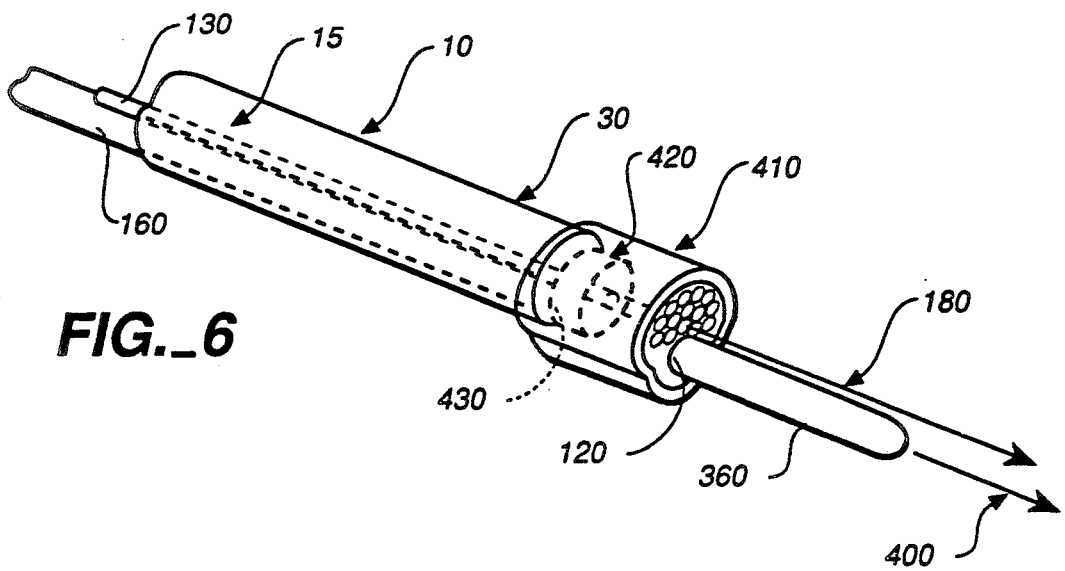
FIG._6

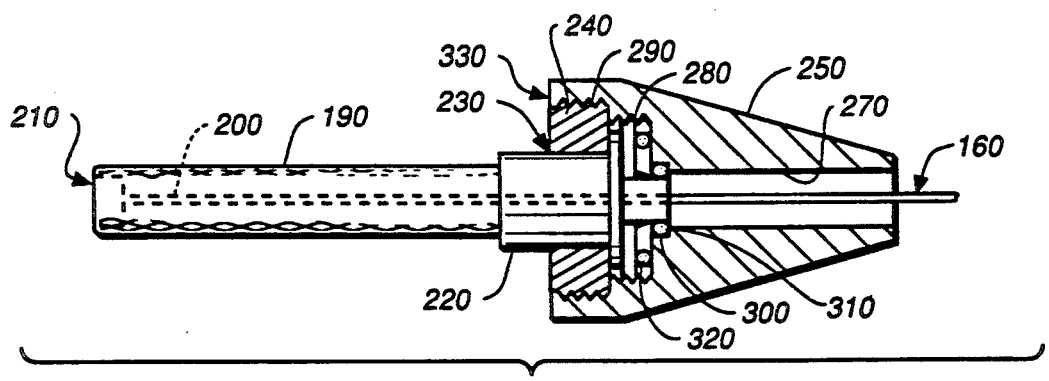
FIG._7
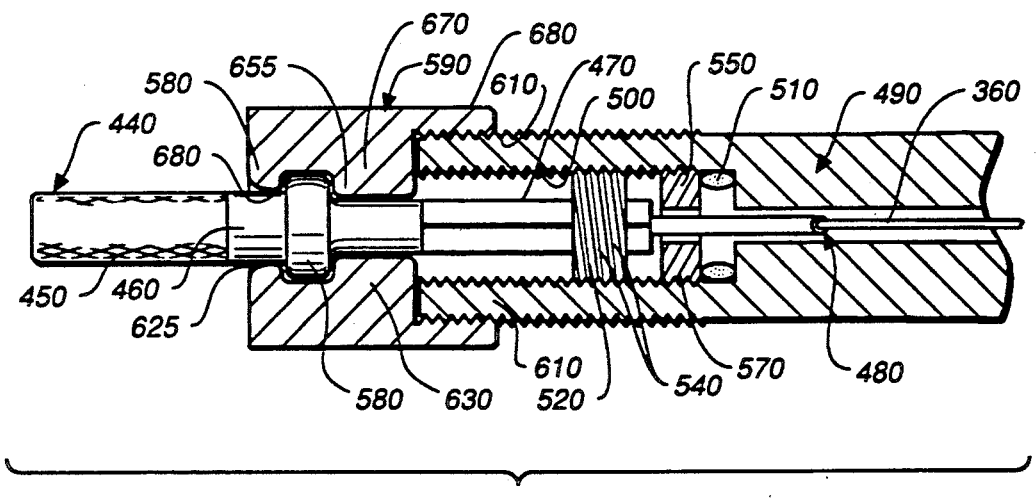
FIG._8
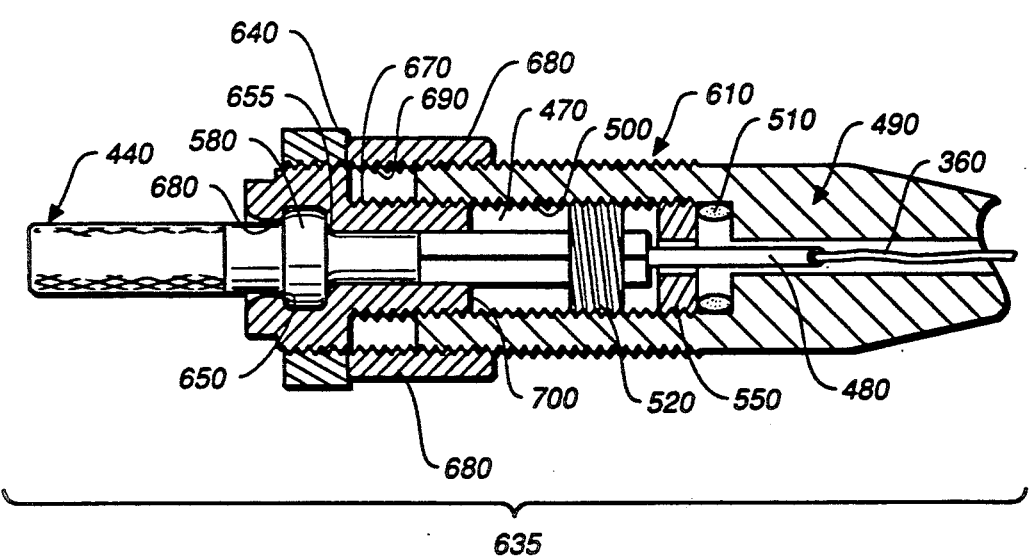
FIG._9

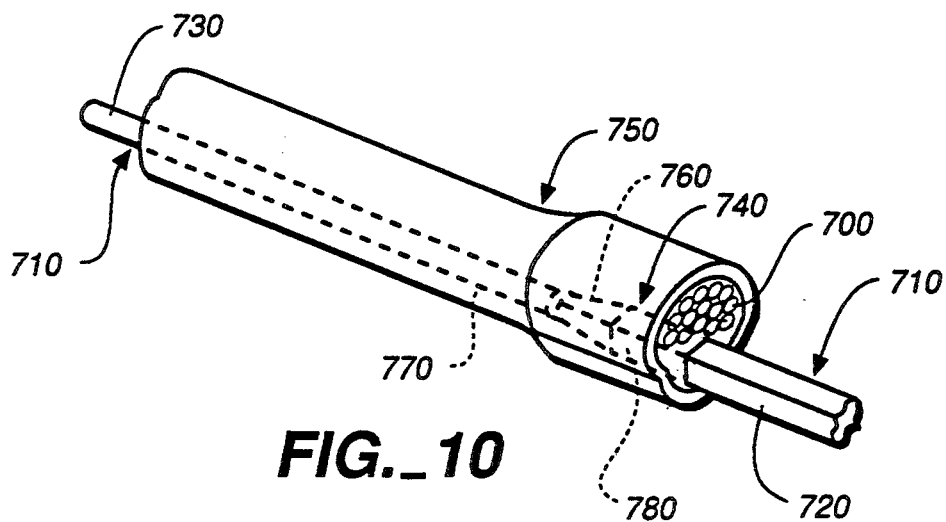
FIG._10
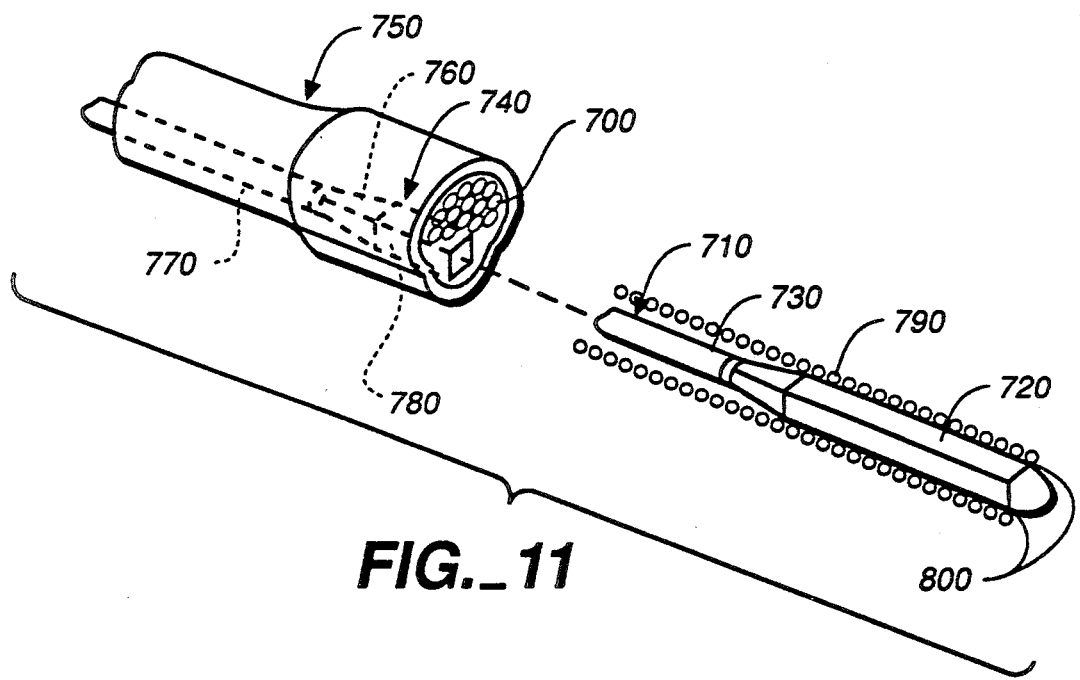
FIG._11
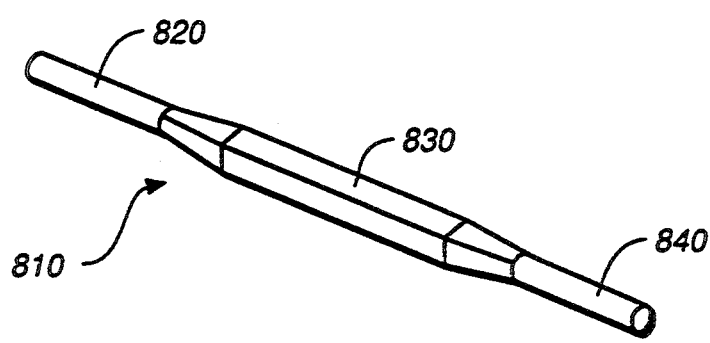
FIG._12

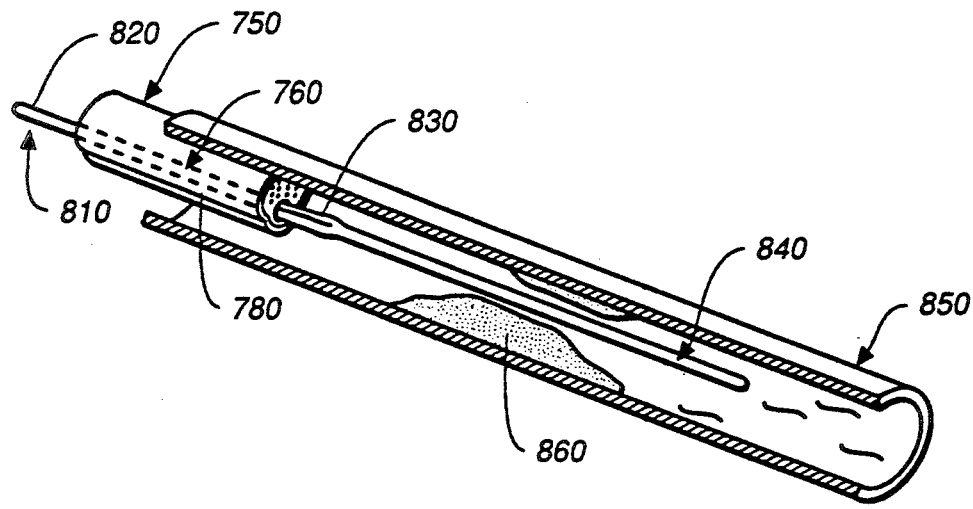
FIG._13
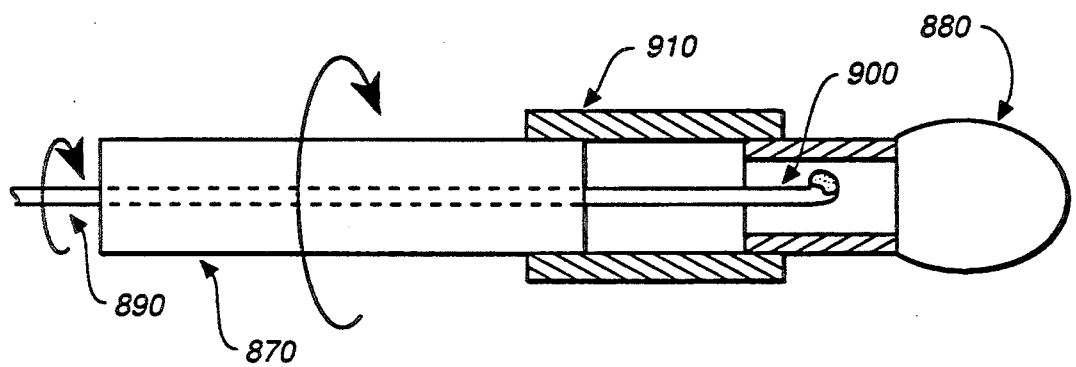
FIG._14
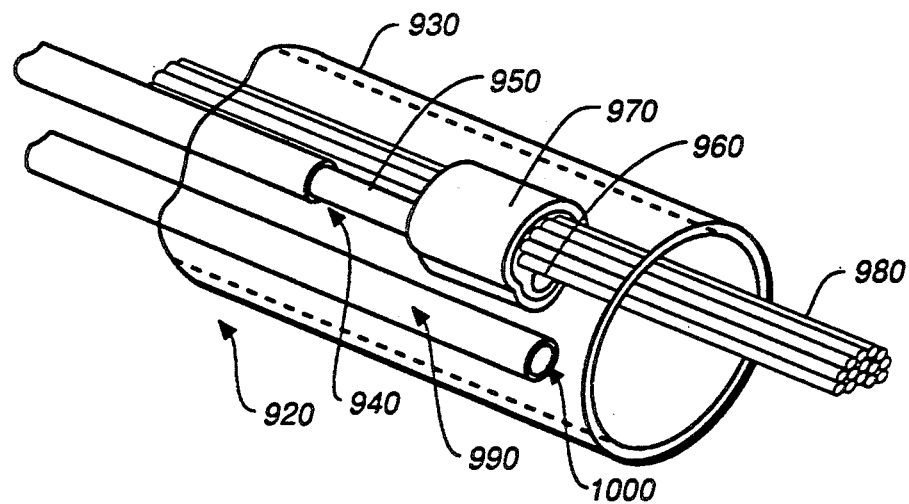
FIG._15

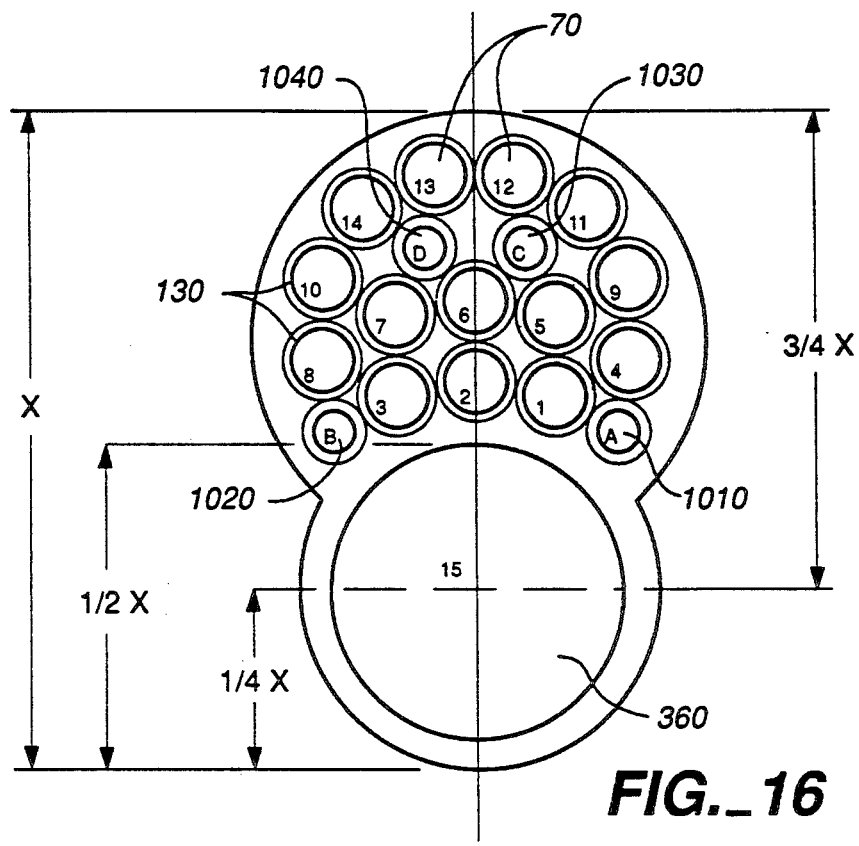
FIG._16
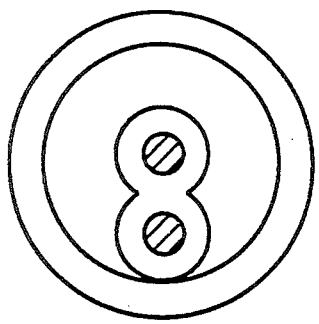
FIG._15A
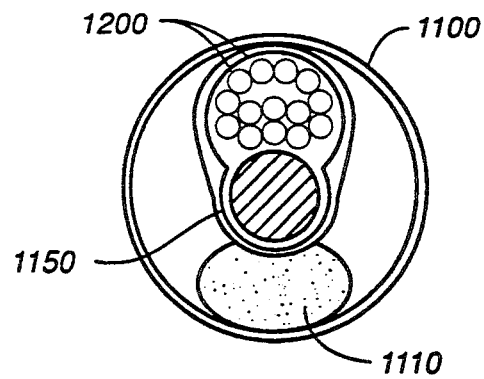
FIG._21
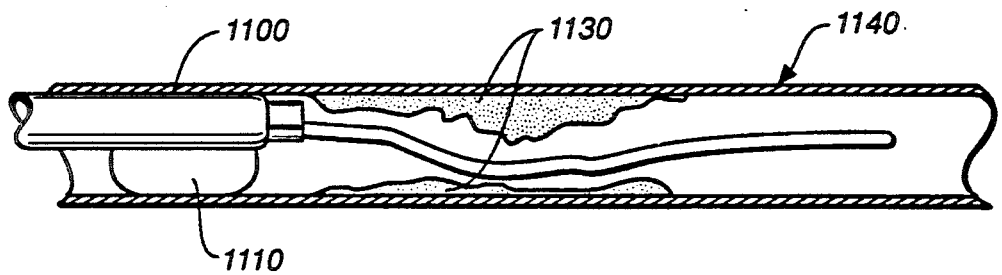
FIG._20

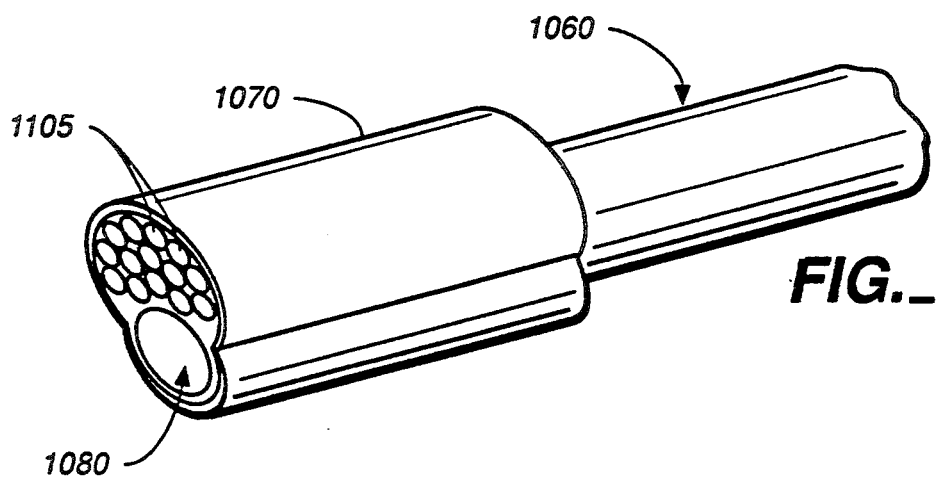
FIG._17
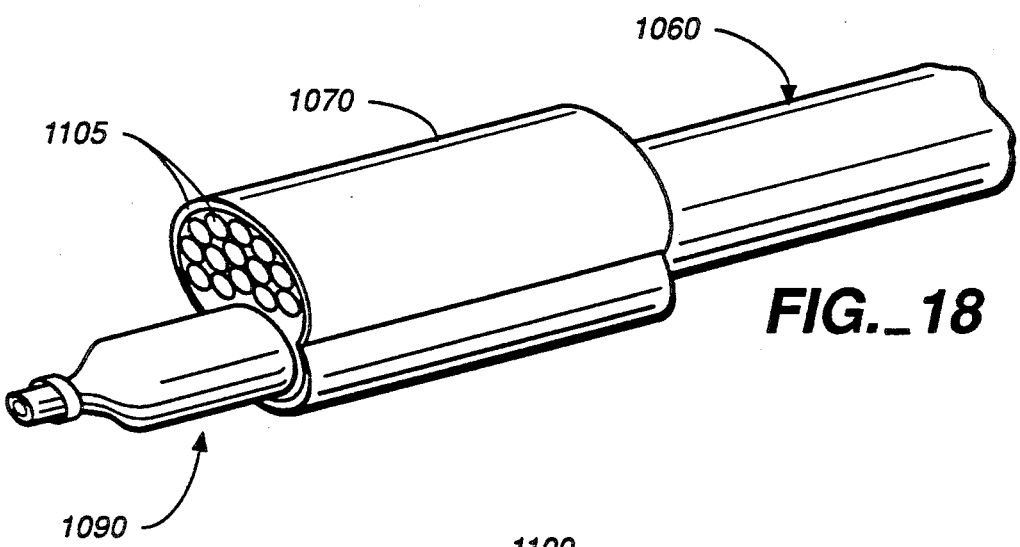
FIG._18
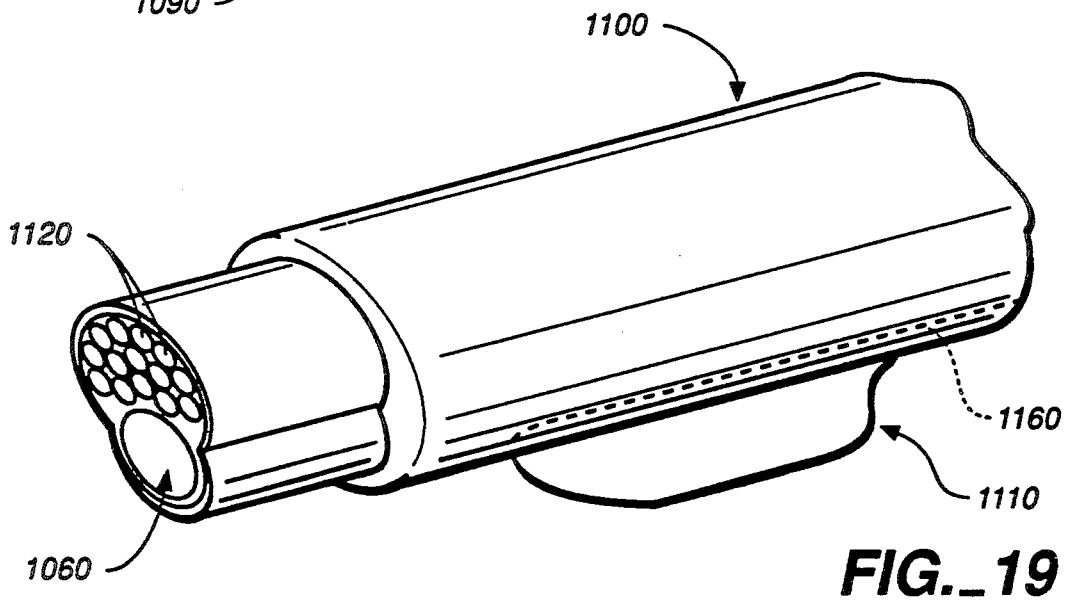
FIG._19

CATHETER TORQUE MECHANISM

BACKGROUND OF THE INVENTION

This method relates generally to medical catheters, and in particular to a new torque control and rotation limiting mechanism for manipulating the tip of such a catheter by rotating it within a patient's body. Typically, a medical catheter is introduced into a patient and is advanced through paths of variable tortuosity to a treatment site. The path may be fairly straight, or may have many turns in it. The catheter conventionally includes a means for treatment of the patient at a treatment site, such as by balloon dilatation, delivery of mechanical, electromagnetic or laser energy for ablation or removal of atherosclerotic material, angioscopic delivery, delivery of contrast media to tissue at the treatment site, and so on.

In many cases, it is necessary to rotate the catheter tip, either to steer the catheter in a desired direction as it is being introduced into the patient toward the treatment site, or to reposition the catheter tip by rotating it about an axis, thus repositioning the treatment means. Rotation of the catheter tip can be quite difficult. Typically, a medical catheter is designed to be as flexible as possible, in order to allow it to negotiate the curves encountered in the body when positioning the tip at the treatment site, and to make it as atraumatic to the patient as possible. However, the more flexible the catheter, the lower the torsional stiffness will generally be, and thus a compromise must be made between flexibility and stiffness. When the torsional stiffness is low, a single rotation of the proximal end of the catheter may result in less than one full rotation of the distal end of the catheter; for instance, a 360° rotation at the proximal end may result in 180° or less of rotation at the distal end.

Therefore, there is a need for a device which will rotate the tip of a catheter in a reliable manner, and which will minimize the ratio of turns necessary at the proximal end to accomplish a single turn at the distal end.

It is undesirable to twist a catheter too much, since the treatment means, guide wire, fiber optics or other devices within the catheter will become twisted around one another. Thus, there is also a need for a means for limiting the rotational travel of a catheter tip when it is within the patient.

In particular, there is a need for a device wherein no compromise is necessary between the flexibility of the catheter body and the rotational control of the catheter tip.

SUMMARY OF THE INVENTION

In the apparatus of the present invention, a torque wire is affixed to the tip of a catheter, and is rotatably positioned within the catheter body. A rotation mechanism is attached to a proximal end of the torque wire, which extends out of the proximal end of the catheter body, such that rotation of the mechanism transmits rotation along the torsionally stiff but longitudinally flexible torque wire, which, being directly attached to the tip at the distal end of the catheter body, transmits the rotational motion to the tip and to the treatment means, such as fiber optics, carried by the tip. A guide wire lumen is provided in the catheter tip, into which a conventional guide wire loosely fits. In normal usage, the guide wire is first passed into the patient, and is positioned with its distal end adjacent the treatment site. The catheter is then passed over the guide wire, sliding the guide wire through the guide wire lumen. When the catheter tip needs to be rotated, the rotation mechanism handle is turned, which twists the catheter tip around an axis of the guide wire. Preferably, the guide wire lumen is offset from the central axis of the catheter tip and the catheter body, and the torque wire is also offset relative to the central axis. Also, the treatment means in the catheter tip may be offset from the central axis. With this configuration, a full rotation of the rotation handle will result in a rotation of the catheter tip about the offset guide wire axis, causing the treatment means to sweep a larger surface area of the treatment site than the surface area of the catheter tip.

The rotation mechanism includes a Luer body attached to the proximal end of the catheter, and a rotation handle rotatably attached to the Luer body. A threaded nut is attached to the rotation handle, preferably in a slidable manner, and engages internal threads of the Luer body, such that rotation of the handle moves the nut proximally and distally. The threaded nut may be affixed to the handle, or it may be slidably mounted thereon, such that rotation of the handle causes rotation of the threaded nut, but no translational motion of the handle or of the torque wire results. Stops are provided to limit the rotational movement of the handle. An adjustable stop nut may be provided for adjusting travel of the handle nut, and a locking nut may be provided for locking the adjustable stop nut in place.

BRIEF DESCRIPTION OF THE DRAWINGS

FIG. 1 is a perspective view showing a catheter incorporating the apparatus of the present invention.

FIG. 2 is a side view, partly in section, showing detail of the proximal end of the catheter of FIG. 1.

FIG. 3 is a detailed perspective view of the distal end of the catheter, incorporating an alternative to the embodiment of the apparatus of FIG. 1.

FIG. 3A is an end view taken along line 3A—3A of FIG. 3.

FIG. 4 is a detailed view of a portion of the distal end of the catheter of FIG. 1.

FIG. 5 is a view similar to that of FIG. 4, showing the catheter tip attached to the distal end of the catheter.

FIG. 6 shows an alternative embodiment to the catheter tip of FIG. 1.

FIG. 7 is a cross-sectional view of the rotation mechanism of FIG. 1.

FIGS. 8 and 9 are alternative embodiments of the rotation mechanism of FIG. 7.

FIG. 10 shows an embodiment of the invention utilizing a keyed guide wire.

FIG. 11 is an exploded view showing further detail of the embodiment of FIG. 10.

FIG. 12 shows an alternative guide wire for use with the embodiment of FIGS. 10 and 11.

FIG. 13 shows the use of the guide wire of FIG. 12 in situ.

FIG. 14 is a view, partly in cross section, of an alternative embodiment of the invention.

FIG. 15 is a perspective view, partly cut away, of another embodiment of the invention.

FIG. 15A is a simplified end view of the embodiment of FIG. 15.

FIG. 16 is an alternative embodiment of the design shown in FIG. 3A.

FIGS. 17 and 18 show an alternative to the embodiment of FIGS. 3-3A.

FIGS. 19-21 show an alternative to the embodiments of FIGS. 3-3A and 17-18.

DESCRIPTION OF THE PREFERRED EMBODIMENTS

A catheter 10 having a proximal end 20 and a distal end 30 is shown. The proximal end 20 is attached to a triple Y-connector 40 by means of a connector tube 50, which may be of a heat shrink material. (In alternative embodiments, this connector tube may be omitted.) A strain relief tube 60 may also be provided, although this is not separately shown in the sectional view of FIG. 2.

Typically, the catheter body 10 will include a single lumen therethrough, which receives treatment means such as the optical fibers 70 shown in FIGS. 1 and 2. The fibers 70 pass through an optical fiber tube 80, and are affixed in a sealed fashion to the Y-connector 40 by means of potting or other sealing compound 90. It will be appreciated that in FIGS. 1 and 2, certain features are shown which are within the Y-connector 40, such as the tube 80, the potting compound 90 and the optical fibers 70.

In the embodiment of FIG. 1, a catheter tip 100 is attached to the distal end 30 of the catheter 10, such as by means of an adhesive or a heat-shrink tube 110, or by molding. The catheter tip 100 includes multiple lumens, including a guide wire lumen 120, optical fiber lumens 130, and torque wire lumen 140. A radiopaque marker band 150 may be positioned on the distal end 30 for assistance in positioning the catheter tip for fluoroscopy. In a preferred embodiment, the radiopaque marker may be positioned only around the fibers, for indicating rotational position of the catheter tip.

A torque wire 160 is positioned within the catheter lumen 15 and is attached to the tip 100 by a bent-over portion 170, and is fixed in place by an adhesive or other means. The torque wire 160 may alternatively be a cable, a rod of plastic, a flexible drive shaft, or other similar structure. The torque wire 160 has a proximal end extending out of one leg 260 of the Y-connector 40 as shown in FIG. 1. The connection of the torque wire 160 is seen in detail in FIGS. 4 and 5. The torque wire 160 is torsionally stiff, i.e., somewhat resistant to twisting, although it is preferably longitudinally flexible.

As shown in FIGS. 1 and 5, the guide wire lumen 120 is offset from a central axis 180 of the catheter tip and catheter body. In addition, in the preferred embodiment, the torque wire lumen 140 and torque wire 160 are offset from the central axis 180. However, the torque wire alternatively could be positioned along the central axis, and in such an embodiment may serve both as the torque wire and as a guide wire for use in positioning the catheter.

A rotation mechanism 185 includes a torque wire handle 190 connected to the torque wire 160, as shown in FIGS. 1 and 7. The handle 190 includes a lumen 200 therethrough for receiving the torque wire 160, which is affixed at the proximal end of the handle 190 by potting compound 210. The handle 190 includes a portion 220 of enlarged diameter, which preferably has a smooth bearing surface 230. The handle 190 preferably has a knurled or otherwise textured surface for positive gripping.

As shown in FIG. 7, a threaded disk portion or nut 240 is affixed to the handle 190. A swivel housing 250 is connected by friction fit or otherwise to the leg 260 of the Y-connector 40. The swivel housing 250 includes a lumen 270 therethrough for receiving the torque wire 160. The housing 250 further includes interior threads 280 and interior threads 290, which are coaxial with one another and with the lumen 270.

An O-ring 300 is seated in a bore 310 of the swivel housing 250, which closely matches the O-ring in diameter, for forming a seal against the passage of fluid. An O-ring retainer 320 having circumferential threads is threaded into the interior threads 280 until it is adjacent the O-ring 300, for maintaining the O-ring in place.

In assembling the device, the threaded disk portion 240 is threaded into the interior threads 280, and an annular stop 330 with circumferential threads is threaded into the interior threads 290. The interior bore diameter of the stop 330 preferably closely matches the outer diameter of the bearing surface 230.

It will be seen that the apparatus of FIG. 7 causes rotational motion of the handle 190 to be converted to longitudinal translational motion, to the left or right from the point of view of FIG. 7. Also, the stop 330 and the O-ring retainer 320 limit this translational motion, and therefore limit the number of total turns which may be made by the handle 190. The length of the threaded portion 280 of the swivel housing 250 between the stop 330 and the retainer 320 determines the total translational, and hence total rotational, motion of the handle 190.

A fitting such as a Touhy-Borst connector 340 is provided at the central leg of the Y-connector 40. A conventional guide wire 360 is positioned in the guide wire lumen 120, in another guide wire lumen 370 through the Y-connector 40, and in a guide wire lumen (not separately shown) through the Touhy-Borst connector 340.

The apparatus of the invention is used in the following manner. The guide wire 360 is passed into the patient, such that its distal end 380 is near the treatment site. Then, the catheter tip 100 is passed over the guide wire 360, beginning at its proximal end 390, such that the guide wire 360 is received by the guide wire lumen 120, the catheter body lumen 15, the guide wire lumen 370, and the guide wire lumen through the Touhy-Borst connector 340. During this positioning procedure, it may be necessary at times to rotate the tip 100 of the catheter, at which time the handle 190 is rotated, and the rotational motion is transmitted via the torque wire 160 to the catheter tip 100. Such rotation may be necessary, for instance, when an obstruction is encountered by the catheter tip 100, or when a turn is encountered in the patient's vessel.

As the catheter 10 is being positioned over the guide wire 360, rotation of the handle 190 and the torque wire 160 will typically cause the entire catheter 10 to rotate, although there may be a greater degree of twisting at the distal end 30 than at the proximal end 20. This rotation will generally be about an axis 400 of the guide wire 360, although the torque is provided by the offset torque wire 160, because the guide wire 360 is already in place when the catheter 10 is being inserted.

However, when the catheter 10 encounters friction from the vessel walls or other surfaces within the patient, the catheter 10 and the catheter tip 100 will tend to be somewhat firmly fixed, and therefore will not easily rotate. In this case, twisting of the torque wire 160 will tend to cause rotation about the central axis 180 shown in FIG. 1, since less resistance will be provided by rotation of the catheter tip 100 about its own axis than rotation of the catheter tip 100 and the catheter 10 about the offset axis 400. In either case, however, torque is efficiently transmitted to the catheter tip 100, since it is transmitted via the relatively stiff torque wire 160 rather than by the body of the catheter 10.

FIG. 3 shows a catheter tip similar to that of FIG. 1—with the catheter tip 100 omitted for clarity—wherein the torque wire 160 passes substantially into the catheter tip 100. In this embodiment, the marker band 150 is not shown, but it is preferably welded or otherwise adhered to the end of the torque wire. The torque wire 160 in this embodiment may be attached to the catheter tip 100 by bonding it thereto. In addition, the end of the torque wire 160 is preferably flattened or otherwise given a noncircular cross-section, as described below relative to FIGS. 10-13.

FIG. 3A is an end view of the embodiment of FIG. 3, and shows in greater detail the relative positions of the optical fiber lumens 130, the optical fibers 70, and the guide wire 360. In this embodiment, fourteen optical fibers are fixed in an arcuate arrangement by positioning each fiber in a single lumen, where the lumens are in a carefully designed pattern. The guide wire 360 is somewhat eccentrically positioned, as noted above, and the resultant pattern of fibers is such that, when the catheter is rotated about its axis 400 (see FIG. 1), the optical fibers 70 sweep out a circular area, thus evenly distributing the laser beams from the fibers 70 over the treatment area.

The sizes and positions of the lumens, fibers and guide wire in FIG. 3A are to scale, reflecting the particular pattern which has been found to result in a most uniform coverage. It will be noted that the fibers appear in three arcuate rows, of one, five and eight fibers, respectively. The fibers in a given row are positioned as close to one another as possible while maintaining separate lumens, and given the limitations of extrusion of small lumens in a catheter. The fiber lumen walls should be just thick enough to maintain their integrity and to keep the fibers definitely in place.

The arcuate rows of fibers in FIG. 3 and FIG. 3A are formed such that, when the catheter is rotated about the central axis (or such other axis as may be chosen), the paths described by the fiber tips, and hence the paths swept out by the laser beams, are staggered with respect to one another. That is, these paths will overlap just enough to ensure that no portion of the material to be ablated is left untreated, but the overlap will at the same time be minimized to limit the amount of tissue which is subjected to an effective double sweep of laser light. Ideally, there will be substantially no overlap, and the paths described by the fiber tips will just be adjacent to one another. In practice, a certain amount of overlap may be achieved without subjecting a given treatment area to an excess of the laser treatment beam. On the right side of FIG. 3A appears a section of a circle inscribed with arcs of increasing radii, and associated with each arcuate section is a numeral. These numerals represent the actual number of optical fibers which overlap a treatment area in one sweep of the embodiment of FIG. 3A. Thus, no area is swept by more than five fibers (and the five-fiber areas are of minimal size), and generally, each area is swept by no more than three fibers. The sweep pattern shown in FIG. 3A is to the same scale as the end view of the guide wire and fibers in that figure.

FIG. 6 shows an alternative embodiment to the catheter tip 100, comprising a catheter tip 410 which is mounted in a rotatable fashion relative to the distal end 30 of the catheter 10. The catheter tip 410 includes a recess 420 for receiving the distal end 30, and an O-ring 430 is provided for sealing. When the catheter is being positioned, or when it is already positioned such that the catheter tip 410 is adjacent the treatment site, it may be that the catheter encounters a great deal of frictional resistance to rotation. In such a case, rotation of the torque wire 160 will be resisted by the catheter 10, and will instead tend to cause the catheter tip 410 to rotate about the central axis 180 rather than about the axis 400. It will be understood that, since the optical fibers 130 and the torque wire 160 are firmly affixed to the catheter tip 410, although they are loosely positioned within the catheter lumen 15, they will tend to be twisted within the catheter lumen 130 as the catheter tip 410 is rotated relative to the catheter 10. In addition, the guide wire 360 will tend to be rotated as the guide wire lumen 120 rotates about the central axis 180. Thus, it is preferable to provide a certain amount of play of the guide wire lumen 120 relative to the guide wire 360 by making the interior diameter of the guide wire lumen 120 somewhat larger than the exterior diameter of the guide wire 360. A certain amount of rotational motion about the central axis 180 imparted to the guide wire 360 may be acceptable.

The embodiment of FIG. 6 has the advantage that the torque wire positively transmits rotational motion to the catheter tip 410, and, when excessive friction is encountered, the binding effect of the catheter 10 against the patient's vessel does not prevent rotational motion of the catheter tip 410, which automatically rotates independently of the catheter 10, when necessary. Thus, the catheter tip 410 may always be rotationally repositioned, whether for passing an obstruction in the patient's vessel or for redirecting the optical fibers 70 or other treatment means carried by the catheter tip 410 adjacent the treatment site of the patient.

FIG. 8 shows an alternative embodiment of the rotation mechanism shown in FIG. 7. A rotation mechanism 435 is provided, and includes a handle 440 with a knurled portion 450, with the handle preferably having a circular cross section. The handle 440 also includes a smooth portion 460, also preferably having a circular cross section and of the same diameter as the knurled portion 450. The handle 440 further includes a portion 470 of noncircular cross section, and a circular-cross-section distal tip 480. The portions 450, 460 and 470 and the tip 480 include coaxial bores for receiving the torque wire 160. The torque wire 160 is connected to the handle 440 in the same manner as in the embodiment of FIG. 7.

The swivel housing 490 of the embodiment of FIG. 8 is, as in the embodiment of FIG. 1 and 7, connected by friction or otherwise to the leg 260 of the Y-connector 40. The housing 490 includes an interiorly threaded portion 500, with an O-ring 510 positioned at a distal end thereof, for sealing the tip 480 against the passage of fluids.

A nut 520 is slidably positioned over the noncircular portion 470 of the handle 440 and includes an interior bore 530 which closely matches the shape and dimensions of the exterior shape of the noncircular portion 470. The nut 520 includes exterior threads 540, by means of which the nut 520 is threaded into the threaded portion 500.

A stop 550 having exterior threads 560 and an interior bore 570 closely matching the outer diameter of the tip 480 is positioned near the O-ring 510 by threading into the threaded portion 500, and acts to maintain the O-ring 510 in place.

In order to assemble the embodiment of FIG. 8, the nut 520 is then threaded into the threaded portion 500, and the handle 440 is slid over the torque wire 160 (which may already be in place), and the proximal end of the torque wire 160 is affixed to the handle 440, as discussed above. A nut 590 with threads 600 is threaded over exterior threads 610 of the swivel housing 490, and then a bearing hub 580 is positioned over the portion 460 of the handle 440, and is snap-fit into a recess 620 of the nut 590. The recess 620 is preferably defined by annular flanges 625 and 630, with flange 625 being flexible for allowing the bearing hub 580 to be pushed or snap-fit past it when the hub 580 is being positioned. The recess 620—with its annular flanges 625 and 630—and the bearing hub 580 are configured for maintaining the relative longitudinal positions of the handle 440 and the swivel housing 490.

When the handle 440 shown in FIG. 8 is rotated, the nut 520 is thereby also rotated, and is forced by the interiorly threaded portion 500 to move towards the left or right from the point of view of FIG. 8. When the nut 520 reaches the rightmost position, i.e., abutting the stop 550, no further rotational motion of the handle 440 is possible. Likewise, when the nut 520 reaches its leftmost position, adjacent the annular flange 630, no further rotational motion is possible in this direction for the handle 440. This acts as a rotational limitation on the motion of the torque wire 160, and the number of rotations possible may be adjusted by altering the position of the stop 550 within the interiorly threaded portion 500.

The embodiment of FIG. 8 has an advantage over that of FIG. 7, in that rotational motion of the handle 440 is converted into purely rotational motion of the torque wire 160; that is, rotation of the handle 540 does not cause any longitudinal or translational motion of the torque wire 160. In the embodiment of FIG. 7, on the other hand, rotation of the handle 190 causes both translation and rotation of the torque wire 160, which tends to cause tension or stress between the torque wire 160 and the catheter 10, since they are affixed to one another at the catheter tip 100. When the translational motion is small, such as in FIG. 7, where the total number of turns of the handle 190 is limited to approximately two turns, this may not be very significant. However, where larger numbers of rotations are desired, the embodiment of FIG. 8 has the advantage of limiting rotational motion without imparting any translational motion to the torque wire 160.

The rotation mechanism 635 shown in the embodiment of FIG. 9 is in many respects identical to the rotation mechanism 435 shown in the embodiment of FIG. 8, and similar parts are numbered similarly. However, in the mechanism 635, the exterior threads 610 of the swivel housing 490 preferably extend the same distance as the interiorly threaded portion 500. A stop nut 640 is provided, which has a recess 650 bounded by flanges 660 and 665. The bearing hub 580 is press-fit into the recess 650, as in the embodiment of FIG. 8.

The stop nut 640 differs from the nut 590 in several respects, including that it has an exteriorly threaded shaft 670 for threading into the interiorly threaded portion 500. A lock nut 680 having interior threads 690 is threaded over the exterior threads 610. The stop nut 640 may therefore be positioned at any desired longitudinal position relative to the swivel housing 490 simply by rotating it.

The end 700 of the shaft 670 acts as a stop against translational motion to the left of the nut 520. Thus, in order to set the rotational limitations of the handle 440, the nut 680 should be backed off—i.e., rotated such that it moves to the right from the point of view of FIG. 9—and then the stop nut 640 is rotated until the end 700 is the desired distance from the stop 550. Then the lock nut 680 is threaded back to the left until it meets the stop nut 640 in a tight frictional fit, thereby locking it in place.

The embodiment of FIG. 9 has the same general operating function as the embodiment of FIG. 8, with the exception that the limitations on the translational motion of the nut 520, and hence the limitations on the rotational motion of the handle 440 and the torque wire 160, may be adjusted by the user at any time, merely by loosening the lock nut 680, repositioning the stop nut 640, and retightening the lock nut 680.

FIG. 10 shows an embodiment of the invention wherein a guide wire 710 having a distal section 720 having a noncircular cross-section is utilized. The guide wire 710 also has a proximal section 730 having a circular cross-section, and the proximal and distal sections 730 and 720 are either formed in a unitary fashion or are connected at a joint 740. Preferably, the proximal section 730 changes gradually to the shape of the distal section 720, to eliminate corners or other projections.

The catheter 750 of this embodiment includes a guide wire lumen 760 including a first section 770 having a circular cross-section, for receiving the proximal section 730 of the guide wire 710, and also including a second section 780 having a cross-section which matches the noncircular cross-section of the distal section 720 of the guide wire 710.

FIG. 11 is an exploded view of FIG. 10, showing details of the catheter and guide wire. A protective outer spring 790 may be affixed to the guide wire 710, such as by welds or adhesives 800.

FIG. 12 shows an alternative embodiment for a guide wire 810, which includes first, second and third sections 820, 830 and 840, respectively. The guide wire 810 is identical to the guide wire 710, except that the additional section 840 is included, either formed in a unitary fashion with or otherwise attached to the second section 830. The first and third sections 820 and 840 have circular cross-sections, and the second section 830 has a noncircular (such as rectangular or square) cross-section. In an alternative embodiment, not separately shown, the guide wire 810 may be keyed, i.e. have a noncircular cross-section which matches the cross section of the guide wire lumen, along its entire length. This design has the advantage that the catheter may be rotated by means of the guide wire no matter what their relative longitudinal positions, as long as the guide wire is in the keyed portion of the guide wire lumen. The keyed portion of the guide wire lumen is preferably confined to the distal end of the catheter, such that torque applied by the guide wire is transmitted only to the catheter distal end, avoiding the problem of torquing the entire catheter. In certain applications, however, and especially with shorter catheters, it may be advantageous to key the entire guide wire lumen to the shape of the guide wire.

In order to use the embodiment of FIG. 12. the third section 840 of the guide wire 810 is inserted into a vessel 850, as shown in FIG. 13. The guide wire 810 is inserted far enough that the third section 840 is in the desired position, such as adjacent plaque 860 or other undesirable tissue. The catheter 750 is then slid over the guide wire 810, until the second section 780 of the lumen 760 slides over the noncircular cross-section 830 of guide wire 810. At this point, torquing of the guide wire 810 results in rotation of the distal end of the catheter 750, with the keyed cross-sectional shape of the guide wire 810 and the second section 780 of the lumen 760 matching one another closely, such that rotation of the guide wire 810 is imparted to the distal end of the catheter 750. In this way, the fibers 70 may be aimed at any portion of the plaque 860 desired. Thus, the guide wire 810 acts as both a guide wire and a torque wire.

The guide wire 710 may also be utilized in the manner shown in FIG. 13, with the exception that it does not include the most forward portion, i.e., the third section 840. The utilization of the circular forward portion 840 allows penetration past obstructions such as plaque 860 without trauma or damage to tissue within the vessel 850.

An alternative embodiment of the invention which results in some of the advantages of the design of FIG. 6 is shown in FIG. 14, wherein the catheter 870 includes a tip 880 (which may include, for instance, a balloon catheter or other treatment means), and a guide wire 890 is positioned within the catheter 870. The guide wire 890 is affixed at its distal end 900 to the tip 880, such that torque on the guide wire will result in rotation of the tip. In this embodiment, a section 910 is carried by the catheter 870, and in turn carries the catheter tip 880. The section 910 is of a material which is particularly soft or flexible in the circumferential direction, such that rotation of the tip 880 differentially twists or winds up the section 910, without imparting the entire amount of rotation to the catheter 870. In effect, the section 910 is a transition section acting as a rotational buffer between the catheter 870 and the tip 880. Without such a buffer, the torsionally stiffer catheter 870 would tend to rotate more closely with the tip 880 (as it is rotated by the wire 890), thus increasing the amount of torque required for a given rotation of the tip, increasing the difficulty of use of the catheter and decreasing the manipulability of the tip. The design of FIG. 14 may be used with any of the embodiments described herein.

FIG. 15 shows an embodiment of a catheter 920 which greatly reduces the amount of friction on the torque wire over its length. A simplified cross-section of this embodiment is shown in FIG. 15A. In this embodiment, the catheter 920 includes a catheter body 930, within which is positioned a tube 940 of a highly lubricious material (which may or may not be of the same material as the catheter body 930), or having a highly lubricious coating. A torque wire 950 is positioned within the tube 940, and is connected at its distal end 960 to a radiopaque band 970, which may be of gold or another biocompatible metal. The optical fibers 980 are positioned through the band 970, which is thus used to position the fibers by observation on a fluoroscope. As shown in FIG. 15, the band 970 is preferably offset from a central axis of the catheter body 930, to assist the operator of the apparatus in determining the rotational as well as translational position of the fibers 980.

A guide wire tube 990 having a guide wire lumen 1000 is also included in the embodiment of FIG. 15. In an alternative embodiment, not separately shown, the tubes 940 and 990 may be formed as a single, unitary tube having two lumens, one for the torque wire and one for the guide wire. The material for such a tube should be highly lubricious or have a lubricious coating, for the reasons noted above.

FIG. 16, which is drawn to scale, shows an alternative embodiment of the design shown in FIG. 3A, wherein like features are numbered similarly, and wherein the catheter tip 100 is similarly omitted for clarity. The embodiment of FIG. 16 includes additional optical fibers 1010, 1020, 1030 and 1040 positioned as shown, which further assist in ensuring a uniform sweep of the treatment light from the fibers 70. The fibers 70 (numbered 1-14 in FIG. 16) preferably have a diameter of 140 microns, and the fibers 1010-1040 have a diameter of 90 microns. Since the drawings of FIGS. 3A and 16 are to scale, the remaining dimensions can be determined by their relations to these diameters.

FIGS. 17 and 18 shows an embodiment similar to those of FIGS. 3-3A and 16, in that eccentrically placed optical fibers 1050 are utilized, wherein the catheter 1060 includes a tip 1070 with individually extruded lumens for the fibers 1050 and a guide wire lumen 1080. Once the catheter tip 1070 is in place, the guide wire may be removed and a balloon 1090 may be positioned in the lumen 1080. The balloon 1090 is then inflated, thus expanding the catheter tip 1070, which causes the fibers 1050 to separate somewhat from one another, thereby broadening the coverage of the catheter tip 1070, i.e. increasing the area swept by the treatment light from the fibers.

FIG. 19-21 show another embodiment of the invention, wherein the catheter 1100 is essentially like that of FIG. 3, except that a balloon 1110 is positioned along one side of the catheter. Referring to FIG. 20, when the catheter 1100 is placed such that the fibers 1120 are adjacent a treatment site 1130 in a vessel such as artery 1140, the treatment site is partly ablated by application of the treatment means, such as laser light. This results in the partial clearing of the otherwise obstructed treatment site 1130.

As long as the site 1130 is highly occluded, the guide wire 1150 positioned within the guide wire lumen 1160 (shown in FIG. 19) is sufficiently fixed in positioned for the catheter to be stable, allowing for a sure aim of the treatment light at the occlusion. However, as the site becomes cleared (as shown in the lower portion of the artery 1140 in FIG. 20), the guide wire no longer provides so firm an anchor, and it then becomes advantageous to inflate the balloon 110 (by means of a tube 1160 shown in FIG. 19), which props the catheter 1100 against the walls of the artery 1140 as a means for maintaining the fibers 1120 fixed in place for a reliable aim. As with the above embodiments, the catheter 1100 may be rotated for clearing the entire treatment site 1130.

The various features of the alternative embodiments discussed above may be combined with one another with great advantage, although the particular subcombinations are not shown in the figures. It will be appreciated that the above-described invention has significant advantages over earlier designs, among which is the advantage that torque applied at the proximal end of a catheter is transmitted with high efficiency and minimized torsional resistance to the distal end of the catheter, because the structure of the invention avoids transmitting such torque to the catheter body. Additional advantages and variations on the foregoing embodiments may be made without departing from the scope of the invention.

I claim:

1. A torque control mechanism for a catheter, the catheter having a catheter body with a proximal end, a distal end, means positioned near said distal end for treatment of a patient, and a first lumen through the catheter body defining a catheter axis, the torque control mechanism including:

a tip attached to the catheter distal end;

a torque wire having a first end and a second end and positioned in the first lumen with said first end at said catheter proximal end and with said second end affixed to said tip; and means attached to said first end for rotating said torque wire independently of the catheter body, for positioning the treatment means within the patient, wherein said rotating means includes:

a handle and means for attaching said handle to said proximal end said handle being rotatable relative to said attaching means, for allowing rotation of said second end of said torque wire by rotation of said handle, wherein said rotating means further includes means for limiting rotation of said handle relative to said attachment means, wherein said handle includes first coupling means, wherein said attaching means includes a housing connected to the catheter body and having second coupling means coupled with said first coupling means, wherein said first and second coupling means are configured for varying their relative positions when said handle is rotated, said attaching means further including limiting means for defining a range of rotation of said handle, wherein said first coupling means comprises a nut having first threads, said second coupling means comprises second threads carried on said housing, such that rotation of said handle causes said nut to move relative to said housing, and said limiting means comprises a first stop and a second stop positioned at a first and second ends, respectively, of said second coupling means, for preventing threading of said nut past said first and second stops, respectively.

2. The torque control mechanism of claim 1, wherein at least one of said first and second stops is adjustable relative to said second threads, for adjusting said range of rotation of said handle.

3. The torque control mechanism of claim 1, wherein said nut is affixed to said handle.

4. The torque control mechanism of claim 1, wherein said nut is slidably mounted on said handle, and includes a noncircular bore having a shape adjacent to and closely matching an exterior shape of said handle.

* * * * *